United States Patent [19]

Feyen et al.

[11] Patent Number: 4,537,730
[45] Date of Patent: Aug. 27, 1985

[54] PREPARATION OF O,S-DIMETHYL-THIOLOPHOSPHORIC ACID AMIDE

[75] Inventors: Peter Feyen, Mettmann; Hermann Seifert, Cologne; Egon Kohler, Dormagen, all of Fed. Rep. of Germany

[73] Assignee: Bayer Aktiengesellschaft, Leverkusen, Fed. Rep. of Germany

[21] Appl. No.: 516,167

[22] Filed: Jul. 21, 1983

[30] Foreign Application Priority Data

Aug. 3, 1982 [DE] Fed. Rep. of Germany ....... 3228868

[51] Int. Cl.³ .............................................. C07F 9/24
[52] U.S. Cl. ................................... 260/989; 260/979; 260/987
[58] Field of Search ......................... 260/979, 987, 989

[56] References Cited

U.S. PATENT DOCUMENTS

| 2,494,283 | 1/1950 | Cassaday et al. | 260/979 |
| 3,670,057 | 6/1972 | Tsuchiya et al. | 260/987 |
| 3,689,604 | 9/1972 | Schrader et al. | 260/979 |
| 3,832,425 | 8/1974 | Franke | 260/987 |

FOREIGN PATENT DOCUMENTS

| 1077215 | 3/1960 | Fed. Rep. of Germany . |
| 1135905 | 3/1963 | Fed. Rep. of Germany . |
| 1210835 | 2/1966 | Fed. Rep. of Germany . |
| 1246730 | 8/1967 | Fed. Rep. of Germany . |

OTHER PUBLICATIONS

Ex Parte James, 18(9), J.P.O.S., 654–655 (1936).

*Primary Examiner*—Anton H. Sutto
*Attorney, Agent, or Firm*—Sprung, Horn, Kramer & Woods

[57] ABSTRACT

A simplified process for preparing the known insecticide 0,S-dimethylthiolphosphoric acid amide of the formula

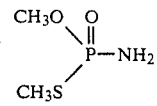

inexpensively, in high purity and with minimum waste water and gas which would have to be specially treated to avoid environmental pollution, comprises
(a) contacting 0,0 dimethyl-thiophosphoric acid amide of the formula

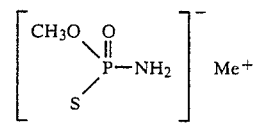

in which
Me is sodium or potassium, separating the aqueous phase,
(b) optionally adding an organic solvent to the aqueous phase, and reacting the mass with methyl bromide or methyl chloride thereby to form the 0,S-dimethyl-thiolphosphoric acid amide, and either
(c) extracting the amide with a sparingly water-miscible solvent thereby to dissolve the amide, or
(d) concentrating the reaction mixture from the methylation step (b), by distillation, until the alkali metal halide formed has separated out, and filtering off the alkali metal halide.

18 Claims, No Drawings

PREPARATION OF O,S-DIMETHYL-THIOLOPHOSPHORIC ACID AMIDE

The invention relates to a new process for the preparation of O,S-dimethyl-thiolophosphoric acid amide. This compound is a highly active insecticide, and is available commercially under the trademarks Tamaron and Monitor (see Pflanzenschutz und Schädlingsbekämpfungsmittel [Plant protection and pest-combating agents] (editor K.-H. Büchel, Stuttgart: Thieme, 1977, page 29). Several possible methods for the preparation of O,S-dimethyl-thiolophosphoric acid amide have already been disclosed, see, for example, German Patent Specification No. 1,668,094, German Patent Specification No. 1,080,109, German Patent Specification No. 1,210,835, German Patent Specification No. 1,246,730, DE-OS (German Published Specification) No. 2,552,945 and DE-OS (German Published Specification) No. 2,135,349). However, the known processes have the disadvantages that the preparation is expensive, the purity of the product obtained is unsatisfactory and/or waste gas and waste water have to be disposed of by means of expensive secondary processes.

It has now been found that the O,S-dimethylthiolophosphoric acid amide of the formula I

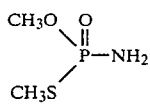

is obtained when
(a) the O,O-dimethyl-thiophosphoric acid amide of the formula II

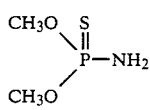

optionally in its crude form from the industrial preparation, is converted with an aqueous solution of KOH or NaOH, in the presence of a sparingly water-miscible organic solvent, to the salt of the formula III

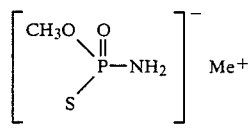

in which
Me represents sodium or potassium, the aqueous phase is separated off and if appropriate the methanol formed is removed from the aqueous phase by distillation, and
(b) the salt of the formula III in the aqueous solution obtained in this manner, if appropriate after the addition of an organic solvent, is converted with methyl bromide or methyl chloride to the compound of the formula I, and either
(c) the compound of the formula I formed in this manner, if appropriate after removal of the organic solvent, is extracted from the aqueous reaction mixture with a sparingly water-miscible solvent in which the compound of the formula I is readily soluble, and the compound of the formula I is isolated in a customary manner, or
(d) the reaction mixture from the methylation stage is concentrated, by distillation, until the alkali metal halide formed has separated out, the alkali metal halide is filtered off, and if appropriate further concentration is carried out or the compound of the formula I is isolated in a customary manner.

It must be regarded as extremely surprising that, using the process according to the invention, the compound of the formula I can be prepared in high purity and yield, even from little-purified starting materials of the formula II which still contain the by-products from the industrial preparation (such as O,O,O-trimethyl thiophosphate). Since it is known that the compound of the formula I is very thermally unstable and can readily react further to give a large number of products, and since it was also to be expected that the salt of the formula III would undergo further hydrolysis and rearrangement reactions, it was in fact to be expected that the desired product (compound of the formula I) would be obtained only in low yield and in poor purity by the route employed.

In addition to the high yield and purity of the end product, the process according to the invention also offers the advantage that it is simple to carry out and produces small amounts of waste water which contain hardly any ammonia and can be readily treated.

The process according to the invention can be illustrated by the following equation (wherein solvent and other reaction parameters are not indicated):

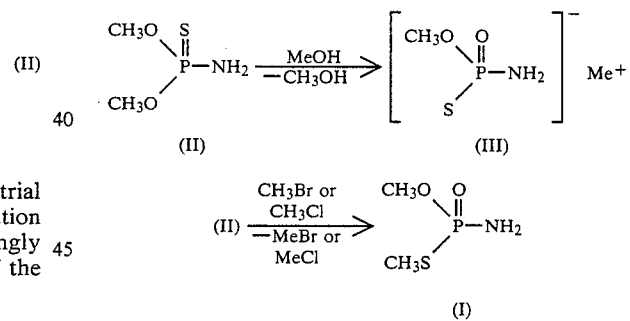

(Me = sodium or potassium)

The starting materials used for the process according to the invention are known. The O,O-dimethyl-thiophosphoric acid amide of the formula II can be of industrial quality and can even contain over 20% of impurities (such as O,O,O-trimethyl thiophosphate). The impurities do not have an adverse effect on the result provided that they exhibit better solubility (which is generally the case) in the organic solvent (in the salt formation) than in the water, and hence are removed with the organic phase.

Suitable organic solvents in the salt formation (process stage (a)) are virtually all sparingly water-miscible organic solvents, such as optionally halogenated aliphatic and aromatic hydrocarbons, and chlorobenzene, xylenes and toluene may be mentioned as examples. For practical reasons, toluene is preferably employed.

For the methylation stage (b), customary organic solvents can be added, and the alcohols having 1 to 6 carbon atoms, preferably methanol, iso-propanol, iso- and n-butanol, may be mentioned as examples.

The reaction temperatures in the salt formation stage (a) are between 30° and 60° C., preferably between 35° and 45° C. and particularly preferably between 38° and 43° C.

The reaction temperatures in the methylation stage (b) are between 45° and 70° C., preferably between 50° and 65° C., and particularly preferably between 53° and 62° C.

The methylation stage (b) is carried out at pH value ranges between 3 and 9, preferably between 4 and 8.5, and particularly preferably between 6 and 8. When methyl chloride is used, a pH value range between 6 and 7 is particularly preferred, and when methyl bromide is used, a range of pH values between 7.5 and 8 is particularly preferred.

The desired pH value can be readily set by the addition of KOH or an acid, such as HCl.

When methyl bromide is used, the methylation stage (b) is advantageously carried out under atmospheric pressure. When methyl chloride is employed, the reaction is advantageously carried out under pressure in a pressure range from 1 to 10 bar, preferably from 2 to 7 bar.

In the salt formation stage (a), equivalent or slightly excess amounts of KOH or NaOH (relative to the compound of the formula II) are used. Preferably 1.0 to 1.2, in particular 1.05 to 1.1, mol equivalents of KOH or NaOH are employed per mol of the compound of the formula II.

In the methylation stage (b), methyl chloride or methyl bromide is employed in equimolar or excess amounts (relative to the compound of the formula II), and excess amounts of up to 30 mol percent can also be used. Preferably 1.0 to 1.25, and particularly preferably 1.05 to 1.2, mols of the methyl halide are used per mol of the compound of the formula II.

In the salt formation stage, the alkali metal hydroxide is preferably employed in an aqueous solution having concentrations of 25 to 60%, in particular of 40 to 58%, by weight.

In this salt formation stage, it is advantageous if the compound of the formula II is present preferably as a 5 to 85% strength, and particularly preferably as a 10 to 80% strength by weight, solution in the sparingly water-miscible organic solvent.

After the salt formation stage, the organic phase, in which the bulk of undesired impurities of the starting material is also present, is separated off in a customary manner.

The methanol formed in the salt formation reaction is, if desired, removed by distillation. For the subsequent methylation reaction, it is advantageous to add an organic solvent. The choice of the concentration of the salt of the formula III in the solvent system water/organic solvent is important for high selectivity in the methylation reaction. Particularly advantageous results are obtained with concentrations between 5 and 60%, in particular between 10 and 50% by weight of salt of the formula III in the reaction medium.

The choice of the ratio of water to organic solvent in the reaction medium is also important in the methylation reaction. Particularly good results are obtained when the ratio water to organic solvent is 100–50%:0–50%, preferably 75–50%:25–50% by weight.

To isolate the compound of the formula I, the organic solvent is removed by distillation after the methylation reaction, provided that this solvent is not also to be used, or cannot also be used, for the subsequent extraction stage. If the subsequent extraction stage is to be carried out using as small volumes as possible, the water can also be completely or partially distilled off. Any alkali metal halide which has separated out can be filtered off.

The compound of the formula I is separated off from the reaction mixture, which if appropriate has been worked up in this manner, by extraction with a suitable organic solvent. For this purpose, it is possible to use all sparingly water-miscible organic solvents in which the compound of the formula I is readily soluble. Higher ketones, such as methyl isobutyl ketone, optionally halogenated aromatic or aliphatic hydrocarbons, such as chloroform, chlorobenzene and toluene, esters, such as ethyl acetate, and higher alcohols, such as n- and i-butanol, may be mentioned as examples. For practical reasons, n- and iso-butanol are particularly preferably used.

The extraction of the compound of the formula I is carried out in a customary manner, for example in several stages.

After the extraction, the organic phase is washed again with water (which can be recycled to the process), and the organic solvent is removed by distillation. The compound of the formula I remains as the residue, in a purity of over 95%, which is sufficient for most purposes, and in yields of over 85% of theory (by repeated extraction of the wash water, the yield can even be increased further), based on the amount of starting compound of the formula II employed.

If a suitable solvent, for example n-butanol, is added at the methylation stage, it is also possible to dispense with the extraction. The reaction mixture is evaporated down (by distillation in vacuo), the mixture is filtered off from the precipitated alkali metal halide, and a solution of the desired product is obtained, which can be concentrated further in a customary manner, or from which the compound of the formula I can be isolated.

However, the extraction method is preferably employed in the process according to the invention.

The examples which follow are intended to illustrate the process according to the invention (all % relate to percentages by weight—unless stated otherwise):

EXAMPLE 1

466.1 g (4.2 mols) of 50.55% strength potassium hydroxide solution are added dropwise to a solution of 613.5 g (4.0 mols) of O,O-dimethyl-thiophosphoric acid amide (technical grade 92%) in 1,078 g of toluene at 40° C., while cooling. The mixture is allowed to react for a further hour at 40° C., and the phases are separated. Approximately 150 g of a mixture of methanol and water are distilled off in vacuo from the aqueous phase. After 1,200 g of n-butanol have been added, 390 g (4.1 mols) of methyl bromide are passed in at 55° C. During this reaction, the pH value is kept between 7.5 and 8. After the reaction is complete, a further 1,200 g of n-butanol are added. Solvent and excess methyl bromide are then distilled off in vacuo until the water content at the bottom has reached ≦0.2% (according to K. Fischer). The solution is filtered off from the precipitated potassium bromide. The residue is washed with 400 g of n-butanol. The combined filtrates are concentrated in vacuo and then analyzed.

The following weight is obtained: 939.1 g of an O,S-dimethyl-thiolophosphoric acid amide solution (n-butanol as solvent)

Content: 59.3% according to HPLC

Yield: 98.7% of theory (relative to O,O-dimethylthiophosphoric acid amide employed)

EXAMPLE 2

The procedure is carried out as described in Example 1, except that n-butanol is replaced by iso-butanol:

Weight: 931.8 g of O,S-dimethyl-thiolophosphoric acid amide solution (iso-butanol as solvent)

Content: 57.5 g according to HPLC

Yield: 94.9 g of theory (relative to O,O-dimethylthiophosphoric acid amide employed).

EXAMPLE 3

The procedure is carried out as described in Example 1, except that n-butanol is replaced by isopropanol.

Weight: 934.6 g of O,S-dimethylthiophosphoric acid amide (isopropanol as solvent)

Content: 57.7% according to HPLC

Yield: 95.6% of theory (relative to O,O-dimethylthiophosphoric acid amide employed).

EXAMPLE 4

The procedure is carried out as described in Example 1, except that potassium hydroxide is replaced by 337.3 g (4.2 mols) of 49.8% strength sodium hydroxide solution.

Weight: 943.6 g of O,S-dimethyl-thiolophosphoric acid amide solution (n-butanol as solvent)

Content: 56.9%

Yield: 95.2% of theory (relative to O,O-dimethyl-thiophosphoric acid amide employed).

EXAMPLE 5

120 g of water are added to a mixture of 161 g of crude O,O-dimethyl-thiophosphoric acid amide which contains 21 g of impurities (such as O,O,O-trimethyl thiophosphate, O,O,S-trimethyl thiophosphate, O-methylthiophosphoric acid amide Na salt and S-methylthiophosphoric acid amide Na salts, etc.) and 208 g of toluene, and the mixture is warmed to 40° C. 1.09 mols of 45% strength sodium hydroxide in water are added dropwise at this temperature, in the course of 10–15 minutes (cooling).

Thereafter, stirring is continued for a further 30 minutes at 40° C., and the organic phase is separated off.

108 g of water and 118 g of methanol are added to the aqueous phase, the pH is adjusted to 6.5 with dilute hydrochloric acid, and the mixture is heated to 60° C. in a pressure-resistant vessel. 58 g of methyl chloride are now pumped into the reactor in the course of 15 minutes with a pump, at the same temperature and the same pH value (with the possible addition of dilute sodium hydroxide solution). A pressure of 6 bar is established, which now gradually decreases to a constant value (about 2 bar) in the course of 2 to 3 hours. To destroy excess methyl chloride and other waste gases, the pressure vessel is released over absorption towers (1. methanolic sodium hydroxide solution, 2. sodium hypochlorite solution).

To work up the O,S-dimethylthiolophosphoric acid amide formed, all of the excess methyl bromide and the methanol, and some of the water, are distilled off in vacuo. The still warm bottom product is now extracted, in a 5-stage extraction, at about 45° C., with the same total amount of iso-butanol relative to the water phase, so that the content of O,S-dimethyl-thiolophosphoric acid amide is <1% in the water phase.

The iso-butanol extracts are washed again with water, and are then completely evaporated down in vacuo, in a 2-stage distillation.

97.3% pure O,S-dimethylthiolophosphoric acid amide is obtained in a yield of 86%. More than 4% of the yield are still in the water phases, of which the rinsing water can be employed in a subsequent mixture to dissolve the sodium chloride formed. A total product yield of over 90% is then obtained.

For relatively small mixtures, it is advisable, as an alternative, also to filter off the sodium chloride under suction after the end of the reaction, and then to carry out the extraction with smaller volumes overall.

It will be understood that the specification and examples are illustrative but not limitative of the present invention and that other embodiments within the spirit and scope of the invention will suggest themselves to those skilled in the art.

What is claimed is:

1. A process for the preparation of O,S-diemthylthiolophosphoric acid amide of the formula

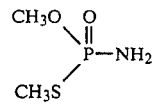

comprising (a) contacting O,O-dimethyl-thiophosphoric acid amide of the formula

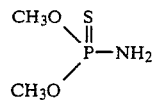

with an aqueous solution of KOH or NaOH, in the presence of a sparingly water-miscible organic solvent selected from the group consisting of chlorobenzene, xylene and toluene, thereby to form the salt of the formula

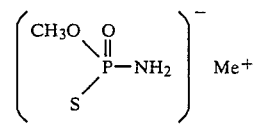

in which

Me is sodium or potassium, separating the aqueous phase, (b) optionally adding an organic solvent to the aqueous phase, and reacting the mass with methyl bromide or methyl chloride thereby to form the O,S-dimethyl-thiolphosphoric acid amide, and (c) extracting the amide with a solvent selected from the group consisting of isobutanol, n-butanol and isopropanol thereby to dissolve the amide.

2. A process according to claim 1, wherein the salt formation reaction (a) is carried out at a temperature between about 30° and 60° C., and the methylation reaction (b) at a temperature between about 45° and 70° C.

3. A process according to claim 1, wherein the methylation reaction (b) is carried out at a pH between about 3 and 9.

4. A process according to claim 1, wherein per mol of starting compound about 1 to 1.2 mol equivalents of KOH or NaOH are used in the salt formation reaction (a), and about 1.0 to 1.25 mols of methyl chloride or methyl bromide are used in the methylation chloride or methyl bromide are used in the methylation reaction (b).

5. A process according to claim 1, wherein toluene is used as the sparingly water-miscible organic solvent in the salt formation stage (a).

6. A process according to claim 1, wherein an alcohol having 1 to 6 carbon atoms is added as organic solvent in the methylation stage (b).

7. A process according to claim 1, wherein n- or iso-butanol is added as organic solvent in the methylation stage (b).

8. A process according to claim 5, wherein n- or iso-butanol is added as organic solvent in the methylation stage (b).

9. A process according to claim 8, wherein the O,O-dimethyl-thiophosphoric acid amide contains some by-product O,O,O-trimethyl thiophosphate.

10. A process for the preparation of O,S-dimethylthiolophosphoric acid amide of the formula

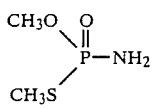

comprising (a) contacting O,O-dimethyl-thiophosphoric acid amide of the formula

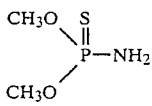

with an aqueous solution of KOH or NaOH, in the presence of a sparingly water-miscible organic solvent selected from the group consisting of chlorobenzene, xylene and toluene, thereby to form the salt of the formula

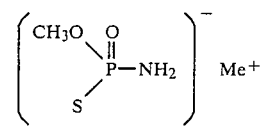

in which

Me is sodium or potassium, separating the aqueous phase, (b) optionally adding an organic solvent to the aqueous phase, and reacting the mass with methyl bromide or methyl chloride thereby, to form the O,S-dimethyl-thiolphosphoric acid amide, and (c) concentrating the reaction mixture from the methylation step (b), by distillation, until the alkali metal halide formed has separated out, and filtering off the alkali metal halide.

11. A process according to claim 10, wherein the salt formation reaction (a) is carried out a temperature between about 30° and 60° C., and the methylation reaction (b) at a temperature between about 45° and 70° C.

12. A process according to claim 10, wherein the methylation reaction (b) is carried out at a pH between about 3 and 9.

13. A process according to claim 10, wherein per mol of starting compound about 1 to 1.2 mol equivalents of KOH or NaOH are used in the salt formation reaction (a), and about 1.0 to 1.25 mols of methyl chloride or methyl bromide are used in the methylation chloride or methyl bromide are used in the methylation reaction (b).

14. A process according to claim 10, wherein toluene is used as the sparingly water-miscible organic solvent in the salt formation stage (a).

15. A process according to claim 10, wherein an alcohol having 1 to 6 carbon atoms is added as organic solvent in the methylation stage (b).

16. A process according to claim 10, wherein n- or iso-butanol is added as organic solvent in the methylation stage (b).

17. A process according to claim 14 wherein n- or iso-butanol is added as organic solvent in the methylation stage (b).

18. A process according to claim 17, wherein the O,O-dimethyl-thiophosphoric acid amide contains some by-product O,O,O-trimethyl thiophosphate.

* * * * *